United States Patent [19]

Brombacher et al.

[11] Patent Number: 4,711,889
[45] Date of Patent: Dec. 8, 1987

[54] SCHISTOSOMICIDAL ACRIDANONE HYDRAZONES

[75] Inventors: Urs Brombacher, Riehen; Helmut Link; Marc Montavon, both of Basel, all of Switzerland

[73] Assignee: Hoffman-La Roche Inc., Nutley, N.J.

[21] Appl. No.: 887,580

[22] Filed: Jul. 18, 1986

Related U.S. Application Data

[63] Continuation of Ser. No. 551,808, Nov. 15, 1983, abandoned.

[51] Int. Cl.$^4$ .................... A61K 31/47; C07D 219/10
[52] U.S. Cl. .................................. 514/297; 514/225; 514/230; 514/231; 544/126; 544/361; 546/106
[58] Field of Search ............... 546/106; 544/126, 361, 544/60; 514/297, 225, 230, 231

[56] References Cited

U.S. PATENT DOCUMENTS 3,712,943 1/1973 Mayer et al. .................. 424/257 X
3,936,444 2/1976 Botts ................................ 546/162
4,544,659 10/1985 Brombacher et al. ............ 514/297

FOREIGN PATENT DOCUMENTS 0094982 10/1922 Switzerland ...................... 546/105
0096608 11/1922 Switzerland ...................... 546/105
1068595 5/1967 United Kingdom .

OTHER PUBLICATIONS

Hünig, et al., Chemical Abstracts, vol. 55, 12857h–12859f (1961).
Zhang, et al., Chemical Abstracts, vol. 93, 239185w (1980).
Ioffe, et al., Chemical Abstracts, vol. 71, 61177a (1969).
Ioffe, et al., Chemical Abstracts, vol. 71, 70475y (1969).
Elslager, et al., Chemical Abstracts, vol. 72, 3335k (1970).

*Primary Examiner*—Donald G. Daus
*Assistant Examiner*—Diana G. Rivers
*Attorney, Agent, or Firm*—Jon S. Saxe; Bernard S. Leon; Matthew Boxer

[57] ABSTRACT

The invention relates to acridanone derivatives of the formula

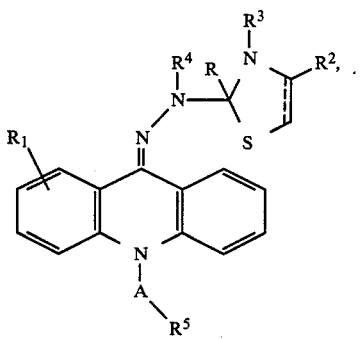

wherein the dotted line is an optional bond,
$R^1$ is hydrogen, halogen or nitro,
$R^2$ is hydrogen or lower alkyl,
one of $R^3$ and $R^4$ is hydrogen or lower alkyl and the other together with R is an additional bond,
A is lower alkylene,
$R^5$ is a 5-membered nitrogen-containing, optionally lower alkyl-substituted aromatic heterocycle, amino or the group

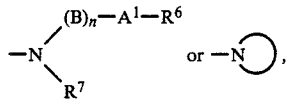

the symbol

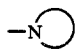

is a 5- or 6-membered, optionally lower alkyl-substituted saturated heterocycle which can contain as a ring member oxygen or sulfur or the group >NH or >N(B)$_n$—A$^1$—R$^6$, B is the group —CO—, —COO— or —SO$_2$—, n is the number 0 or 1, A$^1$ is lower alkylene, R$^6$ is hydrogen, amino, lower alkylamino or di(lower alkyl)amino and R$^7$ is hydrogen or lower alkyl, and pharmaceutically acceptable acid addition salts thereof, their preparation and pharmaceutical compositions based thereon.

34 Claims, No Drawings

SCHISTOSOMICIDAL ACRIDANONE HYDRAZONES

This is a continuation of application Ser. No. 551,808, filed Nov. 15, 1983, now abandoned.

BRIEF SUMMARY OF THE INVENTION

The invention relates to acridanone derivatives of the formula

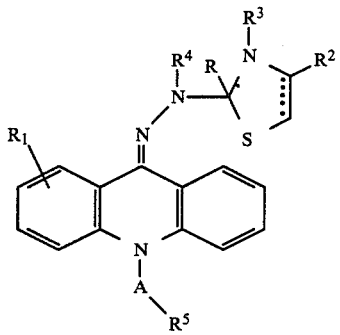

wherein the dotted line is an optional bond, $R^1$ is hydrogen, halogen or nitro, $R^2$ is hydrogen or lower alkyl, one of $R^3$ and $R^4$ is hydrogen or lower alkyl and the other together with R is an additional bond, A is lower alkylene, $R^5$ is a 5-membered nitrogen-containing, optionally lower alkyl-substituted aromatic heterocycle, amino or the group

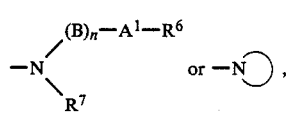

the symbol

is a 5- or 6-membered, optionally lower alkyl-substituted saturated heterocycle which can contain as a ring member oxygen or sulfur or the group >NH or >N(B)$_n$—A$^1$—R$^6$, B is the group —CO—, —COO— or —SO$_2$—, n is the number 0 or 1, A$^1$ is lower alkylene, $R^6$ is hydrogen, amino, lower alkylamino or di(lower alkyl)amino and $R^7$ is hydrogen or lower alkyl, and pharmaceutically acceptable acid addition salts thereof.

In another aspect, the invention relates to intermediates of the formula

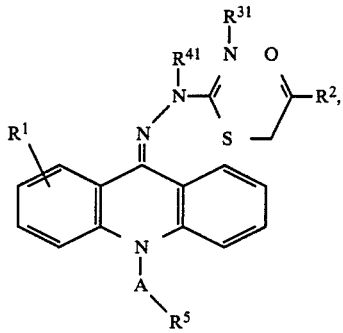

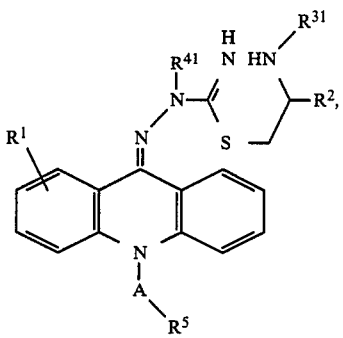

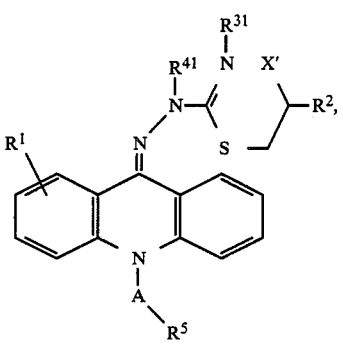

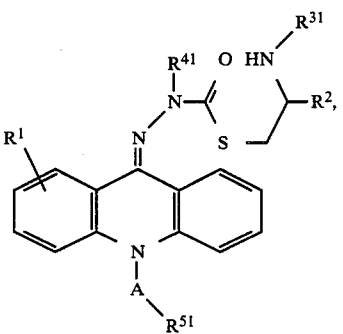

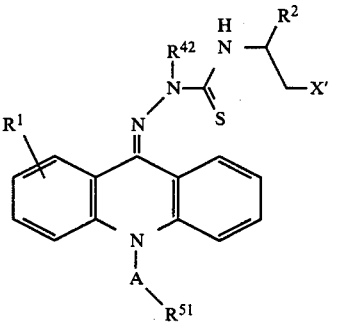

-continued

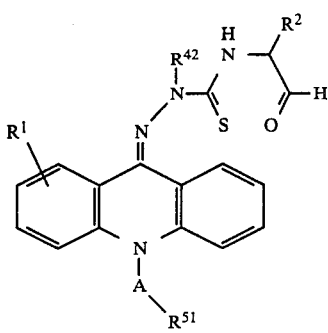

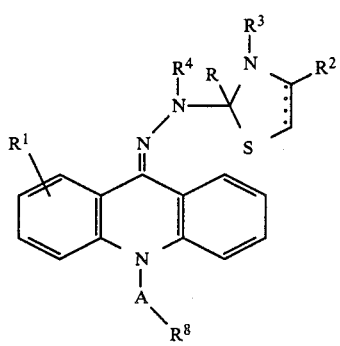

wherein R¹, R², R⁴, R⁵, R⁸, R³¹, R⁴¹, R⁴² or R⁵¹ are as hereinafter described.

In yet another aspect, the invention relates to a process for the preparation of the compounds of formula I.

DETAILED DESCRIPTION OF THE INVENTION

The invention relates to acridanone derivatives of the formula

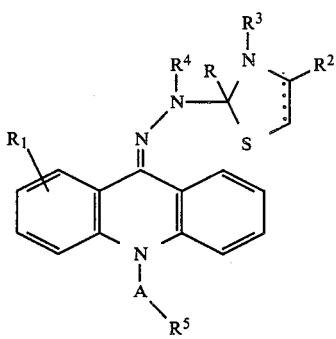

I wherein the dotted line is an optional bond,
R¹ is hydrogen, halogen or nitro,
R² is hydrogen or lower alkyl,
one of R³ and R⁴ is hydrogen or lower alkyl and the other together with R is an additional bond,
A is lower alkylene,
R⁵ is a 5-membered nitrogen-containing, optionally lower alkyl-substituted aromatic heterocycle, amino or the group

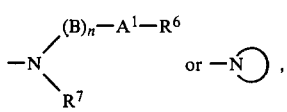

the symbol

VII is a 5- or 6-membered, optionally lower alkyl-substituted saturated heterocycle which can contain as a ring member oxygen or sulfur or the group >NH or >N(B)$_n$—A¹—R⁶, B is the group —CO—, —COO— or —SO$_2$—, n is the number 0 or 1, A¹ is lower alkylene, R⁶ is hydrogen, amino, lower alkylamino or di(lower alkyl)amino and R⁷ is hydrogen or lower alkyl, and pharmaceutically acceptable acid addition salts thereof.

The compounds of formula I possess valuable pharmacological properties and can be used in the control or prevention of illnesses.

Objects of the invention are acridanone derivatives of formula I and their pharmaceutically acceptable salts, the preparation of said compounds and salts, intermediates for their preparation, medicaments containing the compounds of formula I or salts thereof and the preparation of said medicaments.

Depending on the significance of the dotted line and of substituents R, R³ and R⁴, the compounds of formula I above can be present in various tautomeric forms. The invention includes all possible tautomeric forms.

As used herein, the term "lower" denotes groups which contain up to 7, preferably up to 4, carbon atoms and can be straight-chain or branched-chain. The term "lower alkyl" denotes saturated hydrocarbon groups such as methyl, ethyl, propyl, isopropyl, n-butyl, n-pentyl and the like. The term "lower alkylene" denotes divalent hydrocarbon groups such as methylene, dimethylene, trimethylene, 1,2-propylene, 1,4-butylene, 1,5-butylene and the like. The term "halogen" denotes fluorine, chlorine, bromine or iodine.

The term "5-membered, nitrogen-containing aromatic heterocycle" denotes heterocycles containing one or two hetero atoms, when two hetero atoms are present, one hetero atom can be different from nitrogen and can be, for example, oxygen or sulfur. The heterocycles can be linked with group A via a carbon atom or, if desired, via a nitrogen atom of the heterocycle. The following are examples of heterocycles: 1-methyl-4-imidazolyl, 2-pyrrolyl, 2-thiazolyl, 4-oxazolyl, 1-pyrazolyl, 3-isoxazolyl and the like.

The term "5- or 6-membered saturated heterocycle which can contain as a ring member an oxygen or sulfur atom or the group >NH or >N(B)$_n$—A¹—R⁶" denotes 5- or 6-membered saturated heterocycles which contain only one hetero atom, namely a nitrogen atom, such as, 1-pyrrolidinyl and 1-piperidinyl, or which contain two hetero atoms, that is, one nitrogen atom and, in addition, one oxygen, sulfur or nitrogen atoms, such as, 4-morpholinyl, 3-thiazolidinyl and 1-piperazinyl, which can be substituted on the second nitrogen atom by the group —(B)$_n$—A¹—R⁶. As the symbol

indicates, these heterocycles are linked with group A via a nitrogen atom.

The substituent R¹, when it is other than hydrogen, is preferably situated in the 1-position. However, R¹ preferably is hydrogen. R² preferably is hydrogen. Preferably, one of $R^3$ and $R^4$ is hydrogen and the other together with R an additional bond. Preferably A is dimethylene or trimethylene.

$R^5$ preferably is amino, 1-pyrrolidinyl, 1-piperidinyl, 1-morpholinyl, 1-piperazinyl or the group —$NR^7$—$A^1$—$R^{61}$ or

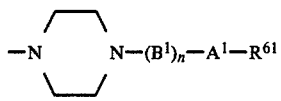

in which $A^1$ is lower alkylene, $B^1$ is the group —CO—, n is the integer 0 or 1, $R^{61}$ is hydrogen and $R^7$ is hydrogen or lower alkyl. Especially preferred groups denoted by $R^5$ are amino, dimethylamino, diethylamino, 1-pyrrolidinyl, 1-piperidinyl, 4-methyl-1-piperazinyl and 4-acetyl-1-piperazinyl.

Especially preferred compounds of formula I are:
10-[2-(4-Methyl-1-piperazinyl)ethyl-9-acridanone (2-thiazolyl)hydrazone,
10-[2-(4-methyl-1-piperazinyl)ethyl]-9-acridanone (2-thiazolidinylidene)hydrazone,
10-[2-(4-acetyl-1-piperazinyl)ethyl]-9-acridanone (2-thiazolidinylidene)hydrazone,
10-[2-(dimethylamino)ethyl]-9-acridanone (2-thiazolidinylidene)hydrazone,
10-[2-(diethylamino)ethyl]-9-acridanone (2-thiazolyl)hydrazone,
10-[2-(1-piperidinyl)ethyl]-9-acridanone (2-thiazolyl)hydrazone,
10-(2-aminoethyl)-9-acridanone (2-thiazolyl)hydrazone,
10-[2-(dimethylamino)ethyl]-9-acridanone (2-thiazolyl)hydrazone,
10-[2-(4-acetyl-1-piperazinyl)ethyl]-9-acridanone (2-thiazolyl)hydrazone,
10-[3-(dimethylamino)propyl]-9-acridanone (2-thiazolyl)hydrazone,
10-[2-(diethylamino)ethyl]-9-acridanone (2-thiazolidinylidene)hydrazone,
10-[2-(1-pyrrolidinyl)ethyl]-9-acridanone (2-thiazolidinylidene)hydrazone and
10-[3-(dimethylamino)propyl]-9-acridanone (2-thiazolidinylidene)hydrazone.

Examples of other compounds of formula I are:
10-[2-(4-Propyl-1-piperazinyl)ethyl]-9-acridanone (2-thiazolidinylidene)hydrazone,
10-[2-(dimethylamino)propyl]-9-acridanone (2-thiazolidinylidene)hydrazone,
10-[2-(1-piperidinyl)ethyl]-9-acridanone (2-thiazolidinylidene)hydrazone,
10-[2-(2,6-dimethyl-1-piperidinyl)ethyl]-9-acridanone (2-thiazolidinylidene)hydrazone,
10-[2-(4-morpholinyl)ethyl]-9-acridanone (2-thiazolidinyldene)hydrazone,
10-[2-(4-ethoxycarbonyl-1-piperazinyl)ethyl]-9-acridanone (2-thiazolidinylidene)hydrazone,
10-[2-(4-pivaloyl-1-piperazinyl)ethyl]-9-acridanone (2-thiazolidinylidene)hydrazone,
10-[2-[4-(methylsulphonyl)-1-piperazinyl]ethyl]-9-acridanone (2-thiazolidinylidene)hydrazone,
10-[(1-methyl-4-imidazolyl)methyl]-9-acridanone (2-thiazolidinylidene)hydrazone,
10-[2-[4-[2-(dimethylamino)acetyl]-1-piperazinyl]-ethyl]-9-acridanone (2-thiazolidinylidene)hydrazone,
1-chloro-10-[2-(diethylamino)ethyl]-9-acridanone (2-thiazolidinylidene)hydrazone,
10-(2-aminoethyl)-9-acridanone (2-thiazolidinylidene)hydrazone,
10-[2-[(methylsulphonyl)amino]ethyl]-9-acridanone (2-thiazolidinylidene)hydrazone,
10-[4-(diethylamino)butyl]-9-acridanone (2-thiazolidinylidene)hydrazone,
10-[5-(diethylamino)pentyl]-9-acridanone (2-thiazolidinylidene)hydrazone,
10-[2-(diethylamino)ethyl]-9-acridanone methyl-(2-thiazolin-2-yl)hydrazone,
10-[2-(diethylamino)ethyl-9-acridanone (3-methyl-2-thiazolidinylidene)hydrazone,
10-[2-(diethylamino)ethyl]-9-acridanone methyl(2-thiazolyl)hydrazone,
10-[2-(4-morpholinyl)ethyl]-9-acridanone (2-thiazolyl)hydrazone,
10-[2-(4-ethoxycarbonyl-1-piperazinyl]ethyl-9-acridanone (2-thiazolyl)hydrazone,
10-[2-(4-pivaloyl-1-piperazinyl)ethyl]-9-acridanone (2-thiazolyl)hydrazone,
10-[2-[4-(methylsulphonyl)-1-piperazinyl]ethyl]-9-acridanone (2-thiazolyl)hydrazone,
10-[2-[4-[2-(diethylamino)ethyl]-1-piperazinyl]ethyl]-9-acridanone (2-thiazolyl)hydrazone and
10-[2-(4-propyl-1-piperazinyl)ethyl]-9-acridanone (2-thiazolyl)hydrazone.

The acridanone derivatives of formula I above and their pharmaceutically acceptable acid addition salts can be prepared in accordance with the invention by
(a) cyclizing a compound of the formula

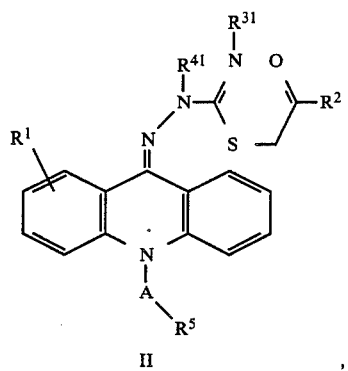

II

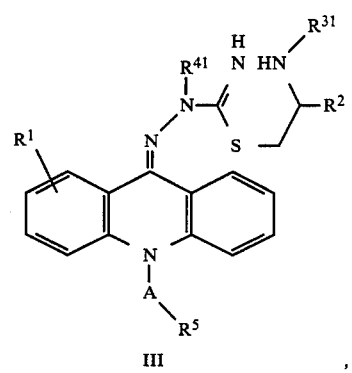

III

-continued

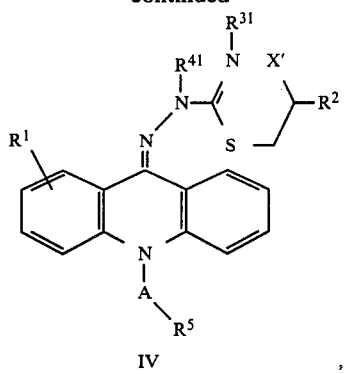
IV

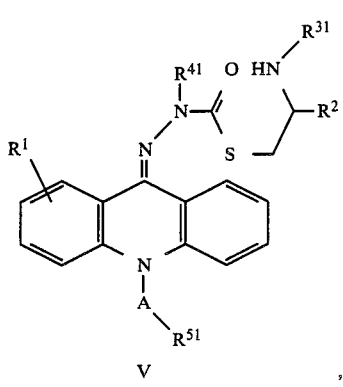
V

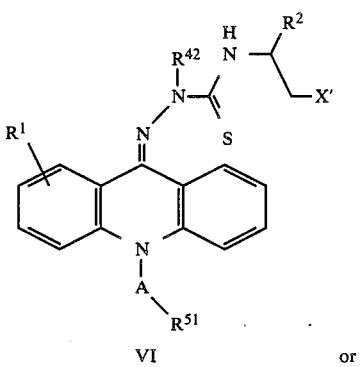
VI or

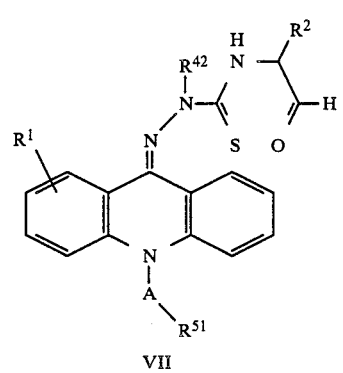
VII wherein one of $R^{31}$ and $R^{41}$ is hydrogen or lower alkyl and the other is hydrogen,
$R^{42}$ is hydrogen or lower alkyl,
$R^{51}$ is a group $R^5$ described above, but which does not contain a primary or secondary basic amino group,
$X'$ is a leaving group and
R, $R^1$, $R^2$ and $R^5$ are as described above, or
(b) reacting a compound of the formula

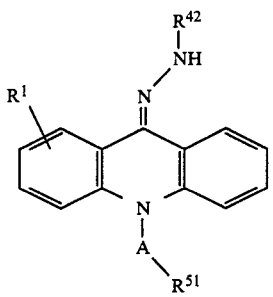
VIII wherein A, $R^1$, $R^{42}$ and $R^{51}$ are as described above, with a compound of the formula

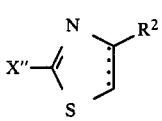
IX wherein $X''$ is a leaving group and the dotted line and $R^2$ are as described above, or
(c) reacting a compound of the formula

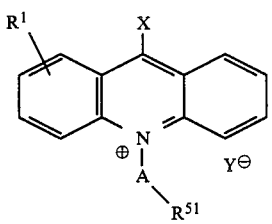
X wherein $Y^{\ominus}$ is an anion, X is a leaving group and A, $R^1$ and $R^{51}$ are as described above, with a compound of the formula

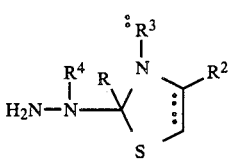
XI wherein the dotted line, R, $R^2$, $R^3$ and $R^4$ are as described above, or
(d) cleaving the N-protecting group in a compound of the formula

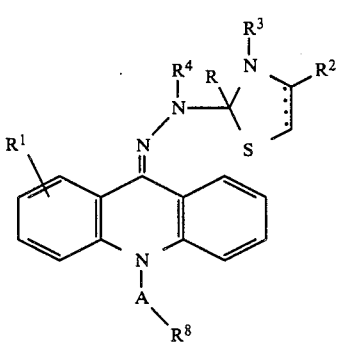
XII wherein $R^8$ is a group $R^5$ as described above which contains a primary or secondary basic amino group blocked by a N-protecting group and the dotted line, R, $R^1$, $R^2$, $R^3$ and $R^4$ are as described above, and (e) if desired, converting a compound of formula I obtained into a pharmaceutically acceptable acid addition salt.

In accordance with process variant (a), the compounds of formula I can be prepared by cyclizing a compound of formula II, III, IV, V, VI or VII according to methods which are known and which are familiar to a person skilled in the art. The leaving group denoted by X' in formulas IV and VI is preferably a halogen atom, especially a bromine or chlorine atom. Depending on the starting material used, the ring closure reaction is carried out fairly readily and can be accomplished or completed, if necessary, by standing for a long time and/or by applying heat. The starting materials for the ring closure reaction need not necessarily be used in isolated form; as a rule it has been found to be convenient to cyclize these starting materials directly or to leave these starting materials to cyclize without isolation from the reaction mixture in which they have been prepared. Depending on the reaction conditions used, in some cases an isolation is not possible, since the cyclization is effected spontaneously.

Suitable solvents for the process variant (a) are, for example, ethers such as tetrahydrofuran, dioxane, ethylene glycol dimethyl ether, diethylene glycol dimethyl ether and the like, alcohols such as methanol, ethanol and the like, dimethylformamide, dimethyl sulfoxide, acetonitrile and the like. The reaction is conveniently carried out at a temperature in the range of about room temperature to the boiling point of the reaction mixture.

In accordance with process variant (b), the compounds of formula I can be prepared by reacting a compound of formula VIII with a compound of formula IX. The leaving group denoted by X'' in formula IX is preferably a halogen atom, for example, chlorine or bromine, or the thiol group. The following organic solvents which are inert under the reaction conditions can be used: ethers such as tetrahydrofuran, dioxane, diethyl ether and the like, alcohols such as methanol, ethanol and the like, dimethylformamide, dimethyl sulfoxide, acetonitrile and the like. The reaction is conveniently carried out at a temperature in the range of about room temperature to the boiling point of the reaction mixture.

In accordance with process variant (c), the compounds of formula I can be prepared by reacting a compound of formula X with a compound of formula XI. The leaving group denoted by X in the compound of formula X is preferably a halogen atom, a lower alkanoyloxy group or a lower alkoxy group, especially a chlorine atom, an acetoxy group or a methoxy group. The compounds of formula X are to some extent substances which are not especially stable. They are therefore conveniently prepared shortly before the reaction with a compound of formula XI from a compound of the formula

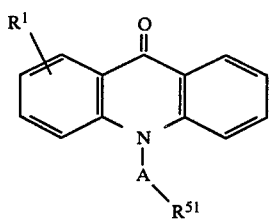

XIV wherein A, $R^1$ and $R^{51}$ are as previously described, as described below and, optionally without previous isolation, processed directly.

The compound of formula XI is conveniently used in the form of an acid addition salt, for example in the form of a hydrochloride or hydrobromide. The reaction can be carried out in the presence of an acid-binding agent, especially suitable acid-binding agents are sodium and potassium carbonates, bicarbonates and acetates. Suitable solvents for process aspect (b) are, for example, lower alcohols such as methanol and ethanol and other organic solvents which are inert under the reaction conditions such as dimethylformamide, acetonitrile and the like. The reaction is conveniently carried out at a temperature in the range of about room temperature to the boiling point of the reaction mixture.

In accordance with process variant (d), the compounds of formula I which contain a primary or secondary basic amino group in the group $R^5$ can be prepared by cleaving the N-protecting group in a compound of formula XII. Suitable protecting groups for the purpose of the present invention are primarily acyl groups, preferably readily cleavable alkoxycarbonyl groups or phenylalkoxycarbonyl groups optionally substituted on the phenyl ring, especially the t-butoxycarbonyl group, the benzyloxycarbonyl group and the like, as well as readily cleavable phenylalkyl groups optionally substituted on the phenyl ring, such as the benzyl group. The cleavage of the protecting group is carried out according to known methods, whereby, of course, the nature of the protecting group to be removed must be taken into consideration when choosing the cleavage method to be used. Likewise, it will, of course, be appreciated that there can be used only those methods which selectively remove the protecting group without affecting other structural elements present in the molecule.

The groups mentioned above as examples of protecting groups can be cleaved hydrolytically. Thus, for example, the benzyloxycarbonyl group and the t-butoxycarbonyl group can be cleaved under selective acidic conditions, for example by treatment with a mixture of hydrogen bromide and glacial acetic acid or by treatment with boron trifluoride or boron tribromide in an inert organic solvent sucn as dichloromethane. The t-butoxycarbonyl group can also be cleaved by treatment with hydrogen chloride in an inert organic solvent such as dioxane, tetrahydrofuran or the like or by treatment with trifluoroacetic acid.

In accordance with process variant (e), the acridanone derivatives of formula I above can be converted into pharmaceutically acceptable acid addition salts. The preparation of such acid addition salts is carried out according to generally known methods. There come into consideration not only salts with pharmaceutically acceptable inorganic acids but also salts with pharmaceutically acceptable organic acids; for example, hydrochlorides, hydrobromides, sulfates, citrates, acetates, succinates, methanesulfonates, p-toluenesulfonates and the like.

The compounds of formula X used as starting materials as well as the compounds of formulas II, III, IV, V, VI, VII, VIII and XII can be prepared from compounds of formula XIII in accordance with the following reaction Scheme in which the dotted line and the substituents A, $R^1$, $R^2$, $R^{31}$, $R^{41}$, $R^{42}$, $R^{51}$, $R^8$, X and X' are as previously described, $R^9$ and $R^{91}$ each is lower alkyl or together is lower alkylene, $R^{52}$ is a group $R^5$ which contains a primary or secondary basic amino group and $R^{10}$ is lower alkyl, phenyl or substituted phenyl. The compounds of formula XIII belong to a class of substance which is known.

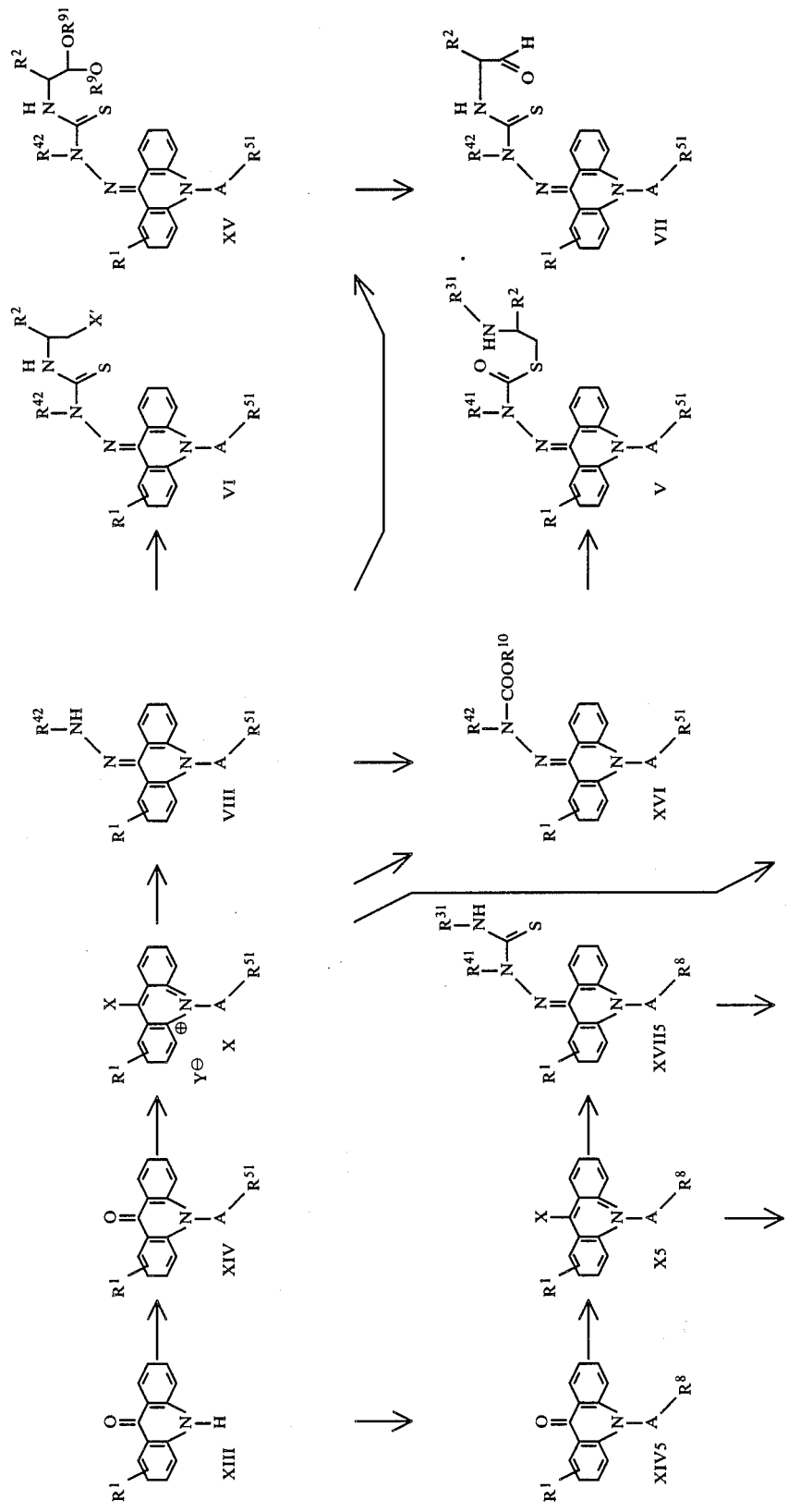

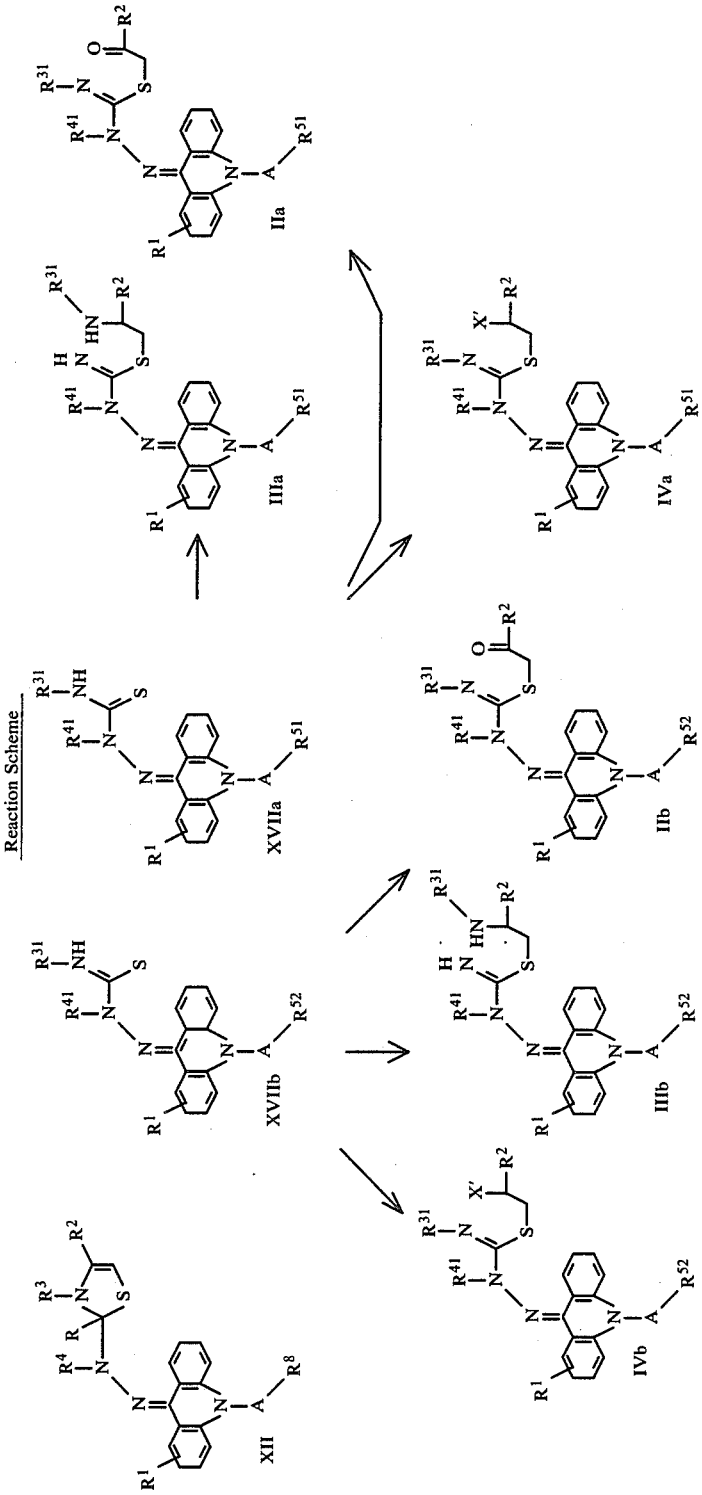

The compounds of formula XIV can be prepared from compounds of formula XIII by alkylation with an agent which yields the group —A—R$^{51}$ in the presence of a strong base such as sodium hydride or the like. This reaction is carried out according to known methods and which are familiar to a person skilled in the art.

Those compounds of formula X in which X is halogen can be prepared by treating a compound of formula XIV in an inert organic solvent with a halogenating agent. In a preferred embodiment, oxalyl chloride or phosphorus oxychloride is used as the halogenating agent and a halogenated hydrocarbon such as methylene chloride, chloroform, 1,2-dichloroethane or the like, acetonitrile or excess halogenating agent is used as the solvent, there is obtained a compound of formula X in which X is chlorine. The reaction temperatures advantageously vary in a range of about room temperature to the boiling point of the reaction mixture.

Compounds of formula X in which X is a leaving group other than halogen can be obtained from the corresponding halogen compounds. For example, the halogen atom in such a compound can be replaced in a known manner by other leaving groups, for example, by lower alkoxy groups or lower alkanoyloxy groups.

The compounds of formula X are quaternary ammonium salts, of which some, as mentioned earlier, are not particularly stable; these are conveniently processed immediately after their preparation. The nature of the anion denoted by Y$^\ominus$ depends on the manner in which the corresponding compound of formula X has been prepared. For example, if a compound of formula X in which X is chlorine is prepared and oxalyl chloride is used as the halogenating agent, then there is obtained a compound of formula X in which Y$^\ominus$ is a chlorine anion; if phosphorus oxychloride is used as the halogenating agent, then there is obtained a corresponding compound in which Y$^\ominus$ is PO$_2$Cl$_2$$^\ominus$.

Those compounds of formula II in which R$^5$ does not contain a primary or secondary basic amino group, that is, compounds of formula IIa, can be prepared by reacting a compound of formula X with a thiosemicarbazide of the formula

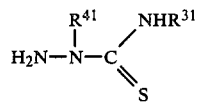   XVIII wherein R$^{31}$ and R$^{41}$ are as previously described, utilizing the reaction conditions described above for process variant (c), and reacting the resulting compound of formula XVIIa with a compound of the formula

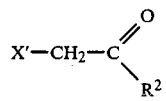   XIX wherein X' and R$^2$ are as previously described. The leaving group denoted by X' is preferably chlorine or bromine. Lower alcohols such as methanol and ethanol are especially suitable solvents. The reaction is conveniently carried out at a temperature in the range of about room temperature to the boiling point of the reaction mixture.

The compounds of formula II in which R$^5$ contains a primary or secondary basic amino group can be prepared by alkylating a compound of formula XIII with an agent which yields the group —A—R$^8$, in analogy to the preparation of a compound of formula XIV, converting the resulting compound of formula XIVS, in analogy to the preparation of the compounds of formula X, into a compound of formula XS, reacting the latter, in analogy to the preparation of the compounds of formula XVIIa, with a thiosemicarbazide of formula XVIII, cleaving the N-protecting group in the resulting compound of formula XVIIS using the reaction conditions described above for process variant (d), and reacting the resulting compound of formula XVIIb with a compound of formula XIX, in analogy to the preparation of the compounds of formula IIa.

The compounds of formula III can be obtained by reacting a compound of formula XVIIa or XVIIb in which R$^{31}$ in each case is hydrogen with a compound of the formula

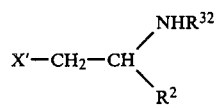   XX wherein X' and R$^2$ are as previously described and R$^{32}$ is hydrogen or, where R$^{41}$ in the compound of formula XVIIa or XVIIb is hydrogen, also lower alkyl.

The amine is conveniently used in the form of an acid addition salt, the hydrochlorides or hydrobromides are preferred. Suitable solvents are, for example, lower alcohols such as methanol and ethanol, ethers such as tetrahydrofuran, dioxane and ethylene glycol dimethyl ether, dimethylformamide, dimethyl sulfoxide, acetonitrile and the like. The reaction is preferably carried out at a temperature between about room temperature and the boiling point of the reaction mixture.

The compounds of formula IV can be obtained by reacting a compound of formula XVIIa or XVIIb in an inert organic solvent and at a temperature in the range of about room temperature to the boiling point of the reaction mixture with a compound of the formula

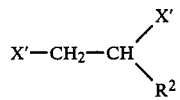   XXI wherein X' and R$^2$ are as previously described, preferably a dichloride or dibromide is utilized. Suitable solvents are, for example, alcohols such as methanol, ethanol and the like, ethers such as tetrahydrofuran, dioxane and the like, dimethylformamide, dimethyl sulfoxide and the like.

The compounds of formula V can be prepared by reacting a compound of formula X with a hydrazine of the formula

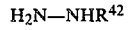   XXII wherein R$^{42}$ are as previously described, utilizing the reaction conditions described above for process variant (c), treating the resulting compound of formula VIII in a known manner with an agent which yields the group —COOR$^{10}$, for example, a dialkyl or diphenyl carbamate or an alkyl or phenyl chloroformate, and reacting the resulting compound of formula XVI with a thiol of the formula

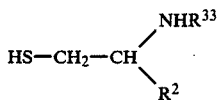

XXIII wherein $R^2$ is as previously described and $R^{33}$ is hydrogen or, where $R^{42}$ in the compound of formula XVI is hydrogen, also lower alkyl.

This third step is preferably carried out at a temperature between about room temperature and the boiling point of the reaction mixture in an inert organic solvent, especially an ether such as diethyl ether, tetrahydrofuran and the like or a lower alcohol such as methanol and ethanol.

Alternatively, the compounds of formula XVI can be prepared by reacting a compound of formula X with a hydrazine of the formula

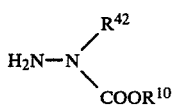

XXIV wherein $R^{42}$ and $R^{10}$ are as previously described.

This reaction can be carried out in a known manner, for example, under the reaction conditions described above for process variant (c).

The compounds of formula VI can be prepared by reacting a compound of formula VIII with an isothiocyanate of the formula

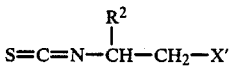

XXV wherein X' and $R^2$ are as previously described.

The reaction can be carried out conveniently at a temperature of about room temperature to the boiling point of the reaction mixture and in an inert organic solvent, for example an ether such as diethyl ether, t-butyl methyl ether and tetrahydrofuran or dimethylformamide, acetonitrile or the like.

The compounds of formula VII can be prepared by reacting a compound of formula VIII with an isothiocyanate of the formula

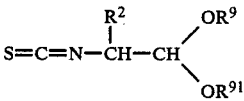

XXVI wherein $R^2$, $R^9$ and $R^{91}$ are as previously described, and subsequently hydrolyzing the acetal group in the resulting compound of formula XV. The first step is conveniently carried out in an inert organic solvent, for example, in an ether such as diethyl ether, t-butyl methyl ether and tetrahydrofuran or in dimethylformamide, acetonitrile or the like, at temperatures between about room temperature and the boiling point of the reaction mixture. The hydrolysis of the acetal group can be carried out by means of an aqueous acid, optionally in the presence of a solubilizer such as tetrahydrofuran, dioxane, methanol, ethanol, dimethylformamide or the like. The acid can be, for example, sulfuric acid, hydrochloric acid, p-toluenesulfonic acid and the like. The temperature is not critical and can vary in a wide range.

As mentioned above, it is not necessary, and in many cases also not possible, to isolate the compounds of formula II, III, IV, V, VI and VII; on the contrary it has been found to be convenient as a rule to cyclize these compounds directly or to allow these compounds to cyclize without isolation from the reaction mixture in which they have been prepared.

The compounds of formula XII used as starting materials can be prepared from compounds of formula XS in analogy to the preparation of the compounds of formula I from compounds of formula X in accordance with process variants (a), (b) and (c) described above and the methods described for the preparation of the corresponding starting materials.

The starting materials of formulas II, III, IV, V, VI, VII and XII are novel and also form objects of the present invention.

The acridanone derivatives of formula I above and their pharmaceutically acceptable acid addition salts possess valuable pharmacological properties; in particular, they possess valuable schistosomicidal activity and can accordingly be used in the control or prevention of schistosomiasis.

The schistosomicidal activity of the acridanone derivatives of formula I and their pharmaceutically acceptable acid addition salts can be demonstrated in an animal test as follows:

Albino mice weighing 15–18 g are infected subcutaneously (sic) with 60±5 cercaria of a Liberia strain of Schistosoma mansoni. Forty six (46) days after the injection, the animals are treated once perorally with the substance to be tested. 5–10 animals are used per substance and dosage. Ten (10) untreated animals serve as controls. The autopsy is carried out after 19 days, whereupon worm pairs and individual worms in the mesenteric veins, portal vein and liver are dissected out and counted. The vermicidal activity shows itself in a reduced number of living parasites in comparison to the number in the control animals.

For the evaluation the percentage reduction in the parasites in treated animals in comparison to untreated control animals is calculated. The $VD_{50}$ is determined according to the Probit method. The $VD_{50}$ is that vermicidal dosage which brings about a 50 percent reduction in the number of worms.

The following Table contains the results obtained with representative compounds of the invention. In the Table there are given for each of listed compounds, the $VD_{50}$ in mg/kg p.o. and the $LD_{50}$ in mg/kg single oral administration to mice.

TABLE

| Compound of formula I | $VD_{50}$ in mg/kg p.o. | $LD_{50}$ in mg/kg p.o. |
| --- | --- | --- |
| 10-[2-Diethylamino)ethyl]-9-acridanone (2-thiazolidinylidene)-hydrazone | 9.5 | 312–625 |
| 10-[3-(Dimethylamino)propyl]-9-acridanone (2-thiazolidinylidene)-hydrazone | 4.7 | 125–250 |
| 10-[2-(4-Methyl-1-piperazinyl)ethyl]-9-acridanone (2-thiazolidinylidene)-hydrazone | 4.0 | 156–312 |
| 10-[2-(Dimethylamino)ethyl]-9-acridanone (2-thiazolidinylidene)hydrazone | 6.4 | 250–500 |
| 10-[2-(1-Pyrrolidinyl)ethyl]-9-acridanone (2-thiazolidinylidene)hydrazone | 6.2 | 156–312 |
| 10-[2-(4-Acetyl-1-piperazinyl)ethyl]-9-acridanone (2-thiazolidinylidene)-hydrazone | 3.4 | 1250–2500 |
| 10-[2-(Diethylamino)ethyl]-9-acrida- | 3.3 | >5000 |

TABLE-continued

| Compound of formula I | VD$_{50}$ in mg/kg p.o. | LD$_{50}$ in mg/kg p.o. |
|---|---|---|
| none (2-thiazolyl)hydrazone/2 HCl | | |
| 10-[3-(Dimethylamino)propyl]-9-acridanone (2-thiazolyl)hydrazone/2 HCl | 3.5 | 312–625 |
| 10-[2-(1-Piperidinyl)ethyl]-9-acridanone (2-thiazolyl)hydrazone/2:3 HCl | 9.0 | 312–625 |
| 10-[2-(4-acetyl-1-piperazinyl)ethyl]-9-(acridanone (2-thiazolyl)hydrazone/2 HCL | 2.6 | 312–625 |
| 10-(2-Aminoethyl)-9-acridanone (2-thiazolyl)hydrazone/2 HCl | 2.6 | 156–312 |
| 10-[2-(Dimethylamino)ethyl]-9-acridanone (2-thiazolyl)hydrazone/2 HCl | 4.9 | 312–625 |
| 10-[2-(4-Methyl-1-piperazinyl)ethyl]-9-acridanone (2-thiazolyl)hydrazone/2:5 HCl | 2.4 | 625–1250 |

The acridanone derivatives of formula I and their pharmaceutically acceptable acid addition salts can be used as medicaments, for example, as pharmaceutical dosage forms. The pharmaceutical dosage forms can be administered orally, for example, as tablets, coated tablets, dragées, hard and soft gelatine capsules, solutions, emulsions or suspensions.

For the preparation of pharmaceutical dosage forms, a acridanone derivative of formula I or a pharmaceutically acceptable acid addition salt can be processed with pharmaceutically inert inorganic or organic carriers. Examples of carriers which can be used for tablets, coated tablets, dragées and hard gelatine capsules are lactose, maize starch or derivatives thereof, talc; stearic acid or its salts and the like. Suitable carriers for soft gelatine capsules are, for example, vegetable oils, waxes, fats, semi-solid and liquid polyols and the like; depending on the nature of the active substance no carriers are, however, generally required in the case of soft gelatin capsules. Suitable carriers for the preparation of solutions and syrups are, for example, water, polyols, saccharose, invert sugar, glucose and the like.

In addition, the pharmaceutical dosage forms can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances.

As mentioned earlier, medicaments containing an acridanone derivative of formula I or a pharmaceutically acceptable acid addition salt thereof also form part of the invention as well as a process for the preparation of such medicaments, which process comprises bringing one or more compounds of formula I or pharmaceutically acceptable acid addition salts thereof and, if desired, one or more other therapeutically valuable substances into a galenical administration form.

As mentioned earlier, the acridanone derivatives of formula I and their pharmaceutically acceptable acid addition salts can be used in the control or prevention of illnesses. More particularly, the acridanone derivatives of formula I and their pharmaceutically acceptable acid addition salts are especially suitable for the control or prevention of schistosomiasis. The dosage at which the compounds of the invention are administration can vary within wide limits and is, of course, fitted to the individual requirements in each particular case. In general, a single dosage of about 1 to about 50 mg/kg body weight should be appropriate for the treatment of schistosomiasis. This dosage can also be administered in sub-divided dosages several times during one day.

The Examples which follow further illustrate the invention in more detail, but are not intended to limit its extent. In the Examples all temperatures are given in degrees Centigrade, unless otherwise stated.

EXAMPLE 1

(a) A mixture of 8.5 g of 9-acridanone, 180 ml of dimethylformamide and 3.3 g of sodium hydride is stirred for 0.5 hour, treated portionwise with 10.3 g of 2-[1-(4-methyl)-piperazinyl]ethyl chloride dihydrochloride, stirred at 80° for 3 days and evaporated. The residue is treated with water and extracted with methylene chloride. The extract is washed with water, dried over sodium sulfate and evaporated, whereupon the residue is recrystallized firstly from ether and then from ethyl acetate. There is obtained 10-[2-(4-methyl-1-piperazinyl)ethyl]-9-acridanone of melting point 156°–157°.

A solution of 2.2 g of 10-[2-(4-methyl-1-piperazinyl)-ethyl]-9-acridanone in 100 ml of dichloromethane is treated portionwise at −5° with 1.17 ml of oxalyl chloride, stirred at room temperature for an additional 0.5 hour and evaporated. The residue (9-chloro-10-[2-(4-methyl-1-piperazinyl)ethyl]-acridinium chloride) is treated with 100 ml of methanol, 1.346 g of 2-hydrazino-2-thiazoline hydrobromide and 1.67 g of sodium acetate, heated to boiling under reflux, cooled after 10 minutes and evaporated. The residue is treated with saturated sodium carbonate solution and extracted with methylene chloride. The extract is washed with water, dried over sodium sulfate and concentrated. After the addition of ethyl acetate, the crystallized-out product is filtered off and washed successively with ethyl acetate and petroleum ether. There is obtained 10-[2-(4-methyl-1-piperazinyl)ethyl]-9-acridanone (2-thiazolidinylidene)hydrazone of melting point 204°–205°.

In an analogous manner there is obtained:

(b) From 9-acridanone and 3-(dimethylamino)propyl chloride, the 10-[3-dimethylamino)propyl]-9-acridanone of melting point 89° and therefrom the 10-[3-(dimethylamino)propyl]-9-acridanone (2-thiazolidinylidene)hydrazone of melting point 191°–192°;

(c) from 9-acridanone and 2-(diethylamino)ethyl chloride hydrochloride, the 10-[2-(diethylamino)ethyl]-9-acridanone of melting point 109°–111° and therefrom the 10-[2-(diethylamino)ethyl]-9-acridanone (2-thiazolidinylidene)hydrazone of melting point 153°–155°;

(d) from 9-acridanone and 2-(1-pyrrolidinyl)ethyl chloride hydrochloride, the 10-[2-(1-pyrrolidinyl)ethyl]-9-acridanone of melting point 143°–145° and therefrom the 10-[2-(1-pyrrolidinyl)ethyl]-9-acridanone (2-thiazolidinylidene)hydrazone of melting point 220° (decomposition);

(e) from 9-acridanone and 2-(1-piperidinyl)ethyl chloride hydrochloride, the 10-[2-(1-piperidinyl)ethyl]-9-acridanone of melting point 165° and therefrom the 10-[2-(1-piperidinyl)-ethyl]-9-acridanone (2-thiazolidinylidene)hydrazone of melting point 207°;

(f) from 9-acridanone and 2-(4-morpholinyl)ethyl chloride hydrochloride, the 10-[2-(4-morpholinyl)ethyl]-9-acridanone of melting point 196° and therefrom the 10-[2-(4-morpholinyl)-ethyl]-9-acridanone (2-thiazolidinylidene)hydrazone of melting point 236°.

EXAMPLE 2

(a) A mixture of 4.5 g of 9-acridanone, 1.1 g of sodium hydride and 100 ml of dimethylformamide is stirred for 0.5 hour, then treated with 5.2 g of 2-(4-acetyl-1-piperazinyl)-ethyl chloride hydrochloride, stirred at 70° for 15 hours and evaporated. The residue is treated with water and extracted with methylene chloride. The extract is washed with water, dried over sodium sulfate and evaporated. By crystallization from ethanol there is obtained 10-[2-(4-acetyl-1-piperazinyl)ethyl]-9-acridanone of melting point 241°–243°.

A suspension of 3.5 g of 10-[2-(4-acetyl-1-piperazinyl)ethyl]-9-acridanone in 100 ml of acetonitrile is treated with 1.7 ml of oxalyl chloride, suction filtered after 0.5 hour and the suction filter material (9-chloro-10-[2-(4-acetyl-1-piperazinyl)ethyl]acridinium chloride) is washed successively with acetonitrile and ether. A mixture of the substance obtained is heated to boiling under reflux with 2 g of 2-hydrazino-2-thiazoline hydrobromide, 2.5 g of sodium acetate and 100 ml of methanol and evaporated after 15 minutes. The residue is treated with water, made alkaline with sodium carbonate solution and extracted with methylene chloride. The extract is washed with water, dried and evaporated, whereupon the residue is crystallized from methanol. After recrystallization from n-butanol, there is obtained 10-[2-(4-acetyl-1-piperazinyl)ethyl]-9-acridanone (2-thiazolidinylidene)hydrazone of melting point 256°.

In an analogous manner there is obtained:

(b) From 9-acridanone and 2-(4-ethoxycarbonyl-1-piperazinyl)ethyl chloride hydrochloride, the 10-[2-(4-ethoxycarbonyl-1-piperazinyl)ethyl]-9-acridanone of melting point 147° and therefrom the 10-[2-(4-ethoxycarbonyl-1-piperazinyl)ethyl]-9-acridanone (2-thiazolidinylidene)hydrazone of melting point 231° (decomposition);

(c) from 9-acridanone and 2-(4-pivaloyl-1-piperazinyl)ethyl chloride hydrochloride, the 10-[2-(4-pivaloyl-1-piperazinyl)ethyl]-9-acridanone of melting point 184° and therefrom the 10-[2-(4-pivaloyl-1-piperazinyl)ethyl]-9-acridanone (2-thiazolidinylidene)hydrazone of melting point 208°;

(d) from 9-acridanone and 2-(4-(methylsulfonyl)-1-piperazinyl]ethyl chloride hydrochloride, the 10-[2-[4-(methylsulfonyl)-1-piperazinyl]ethyl]-acridanone of melting point 244°–246° and therefrom the 10-[2-[4-(methylsulfonyl)-1-piperazinyl]ethyl]-9-acridanone (2-thiazolidinylidene)-hydrazone of melting point 223°–235° (decomposition).

EXAMPLE 3

(a) A mixture of 3.9 g of acridanone, 1.0 g of sodium hydride and 80 ml of dimethylformamide is stirred for 0.5 hours, then treated with 2.9 g of 1-chloro-2-dimethylaminoethane hydrochloride, stirred at 60° for 18 hours and evaporated. The residue is extracted with methylene chloride. The extract is washed with water, dried over sodium sulfate and evaporated. By crystallization from isopropyl ether there is obtained 10-[2-(dimethylamino)ethyl]-9-acridanone of melting point 145°–146°.

A solution of 3 g of 10-[2-(dimethylamino)ethyl]-9-acridanone in 100 ml of dichloromethane and 1.93 ml of oxalyl chloride is stirred for 0.5 hour. After evaporation, the residue is stirred with 2.25 g of 2-hydrazino-2-thiazoline hydrobromide and 3 g of sodium acetate in 100 ml of methanol, whereupon the mixture is heated to boiling under reflux for 10 minutes and evaporated. The residue is treated with water, made alkaline with sodium carbonate solution and extracted with methylene chloride. The extract is washed with water, dried over sodium sulfate and evaporated. After crystallization from acetonitrile, there is obtained 10-[2-(dimethylamino)ethyl]-9-acridanone (2-thiazolidinylidene)-hydrazone of melting point 192°–194°.

In an analogous manner there is obtained:

(b) From 9-acridanone and 2-(dimethylamino)propyl chloride hydrochloride, the 10-[2-dimethylamino)-propyl]-9-acridanone of melting point 114° and therefrom the 10-[2-(dimethylamino)propyl]-9-acridanone (2-thiazolidinylidene)hydrazone of melting point 152°;

(c) from 9-acridanone and 2-(2,6-dimethyl-1-piperidinyl)ethyl chloride hydrochloride, the 10-[2-(2,6-dimethyl-1-piperidinyl)ethyl]-9-acridanone of melting point 146° and therefrom the 10-[2-(2,6-dimethyl-1-piperidinyl)ethyl]-9-acridanone (2-thiazolidinylidene)-hydrazone of melting point 161°;

(d) from 9-acridanone and (1-methyl-4-imidazolyl)-methyl chloride hydrochloride, the 10-[(1-methyl-4-imidazolyl)methyl]-9-acridanone of melting point 205°–207° and therefrom the 10-[(1-methyl-4-imidazolyl)methyl]-9-acridanone (2-thiazolidinylidene)-hydrazone of melting point 206°–208°;

(e) from 9-acridanone and 2-[4-[2-(dimethylamino)acetyl]-1-piperazinyl]ethyl chloride hydrochloride, the 10-[2-[4-[2-(dimethylamino)acetyl]-1-piperazinyl)ethyl]-9-acridanone of melting point 146°–147° and therefrom the 10-[2-[4-[2-(dimethylamino)acetyl]-1-piperazinyl]ethyl-9-acridanone (2-thiazolidinylidene)hydrazone of melting point 129°–131°;

(f) from 1-chloro-9-acridanone and 2-(diethylamino)ethyl chloride hydrochloride, the 10-[2-(diethylamino)ethyl]-1-chloro-9-acridanone of melting point 121° and therefrom the 10-[2-(diethylamino)ethyl]-1-chloro-9-acridanone (2-thiazolidinylidene)hydrazone of melting point 181°–183°;

(g) from 9-acridanone and 2-(4-propyl-1-piperazinyl)ethyl chloride dihydrochloride, the 10-[2-(4-propyl-1-piperazinyl)ethyl]-9-acridanone and therefrom the 10-[2-(4-propyl-1-piperazinyl)ethyl]-9-acridanone (2-thiazolidinylidene)hydrazone of melting point 205°–207° (decomposition).

EXAMPLE 4

A solution of 4.94 g of 10-[2-(diethylamino)ethyl]-9-acridanone in 300 ml of dichloromethane is stirred for 1 hour with 2.85 ml of oxalyl chloride. The resulting salt (9-chloro-10-[2-(diethylamino)ethyl]acridinium chloride) is filtered and treated with 100 ml of methanol, 2.82 g of 2-(3-methyl)thiazolidinylidenehydrazine hydrochloride and 4.1 g of sodium acetate. The mixture is heated to boiling under reflux for 10 minutes and evaporated. The residue is treated with water, made alkaline with sodium carbonate solution and extracted with dichloromethane. The extract is washed with water, dried and evaporated. By crystallization from ethanol there is obtained 10-[2-(diethylamino)ethyl]-9-acridanone (3-methyl-2-thiazolidinylidene)hydrazone of melting point 123°–125°.

EXAMPLE 5

(a) A solution of 11.5 g of 10-[2-(diethylamino)ethyl]-9-acridanone in 250 ml of dichloromethane is treated at −5° and within 0.5 hour with 6.7 ml of oxalyl chloride, stirred at room temperature for 1 hour, the yellow crystals (9-chloro-10-[2-(diethylamino)ethyl]acridinium chloride) which have formed are filtered and washed successively with methylene chloride and petroleum ether. The material obtained is taken up in 200 ml of methanol, treated with 3.6 g of thiosemicarbazide and stirred at room temperature for about 18 hours. The precipitated salt is filtered and washed successively with ethanol and ether. There is obtained 10-[2-(diethylamino)ethyl]-9-acridanone thiosemicarbazone dihydrochloride (crystallizing with 1 mol of methanol) of melting point 124° (decomposition). This material is treated with 1N sodium hydroxide solution and extracted with dichloromethane. The solution is washed with water, dried and evaporated, whereupon the product is crystallized from acetonitrile. There is obtained 10-[2-(diethylamino)ethyl]-9-acridanone thiosemicarbazone of melting point 154°–156°.

A solution of 6.1 g of 10-[2-(diethylamino)ethyl]-9-acridanone thiosemicarbazone in 100 ml of dimethylformamide is stirred for about 18 hours with 4.3 ml of chloroacetaldehyde (50 percent solution in water). The mixture is subsequently evaporated, the residue is taken up in 50 ml of ethanol, made acid to Congo red with ethanolic hydrochloric acid and the crystals formed are filtered. The crystals are washed successively with ethanol, ether and petroleum ether and there is obtained 10-[2-(diethylamino)ethyl]-9-acridanone (2-thiazolyl)hydrazone dihydrochloride of melting point 214°–216° (decomposition).

In an analogous manner there is obtained:

(b) From 10-[2-(1-piperidinyl)ethyl]-9-acridanone and thiosemicarbazide, the 10-[2-(1-piperidinyl)ethyl]-9-acridanone thiosemicarbazone of melting point 187° (decomposition) and therefrom the 10-[2-(1-piperidinyl)ethyl]-9-acridanone (2-thiazolyl)hydrazone 1.5 HCl of melting point 190° (decomposition);

(c) from 10-[2-(4-morpholinyl)ethyl]-9-acridanone and thiosemicarbazide, the 10-[2-(4-morpholinyl)ethyl]-9-acridanone thiosemicarbazone of melting point 240° (decomposition) and therefrom the 10-[2-(4-morpholinyl)ethyl]-9-acridanone (2-thaizolyl)hydrazone dihydrochloride of melting point 225° (decomposition);

(d) from 10-[2-(4-acetyl-1-piperazinyl)ethyl]-9-acridanone and thiosemicarbazide, the 10-[2-(4-acetyl-1-piperazinyl)ethyl]-9-acridanone thiosemicarbazone of melting point 225° (decomposition) and therefrom the 10-[2-(4-acetyl-1-piperazinyl)ethyl]-9-acridanone (2-thiazolyl)hydrazone dihydrochloride of melting point 180° (decomposition);

(e) from 10-[2-(4-pivaloyl-1-piperazinyl)ethyl]-9-acridanone and thiosemicarbazide, the 10-[2-(4-pivaloyl-1-piperazinyl)ethyl]-9-acridanone thiosemicarbazone of melting point 179° (decomposition) and therefrom the 10-[2-(4-pivaloyl-1-piperazinyl)ethyl]-9-acridanone (2-thiazolyl)hydrazone dihydrochloride of melting point 210° (decomposition);

(f) from 10-[3-(dimethylamino)propyl)-9-acridanone and thiosemicarbazide, the 10-[3-(dimethylamino)propyl]-9-acridanone thiosemicarbazone of melting point 202°–204° and therefrom the 10-[3-(dimethylamino)propyl]-9-acridanone (2-thiazolyl)hydrazone dihydrochloride of melting point 195° (decomposition).

EXAMPLE 6

(a) A mixture of 3 g of 10-[2-(4-methyl-1-piprazinyl)ethyl]-9-acridanone, 100 ml of dichloromethane and 1.6 ml of oxalyl chloride is stirred for 0.5 hour, concentrated to half volume and the salt, 9-chloro-10-[2-(4-methyl-1-piperazinyl)ethyl]acridinium chloride, is precipitated by the addition of 100 ml of ethyl acetate. The salt is filtered, washed with petroleum ether and dried. The red-brown powder is heated to boiling under reflux for 5 minutes together with 1.42 g of 2-thiozolyl-hydrazine hydrochloride, 2.3 g of sodium acetate and 100 ml of methanol and then evaporated. The residue is treated with 50 ml of water, made alkaline with sodium carbonate solution and extracted with dichloromethane. The extract is washed with 10 percent sodium chloride solution, dried and evaporated. The residue is taken up in 100 ml of methanol, acidified with ethanolic hydrochloric acid, the precipitated product is filtered and washed successively with a small amount of cold ethanol and petroleum ether. There is obtained 10-[2-(4-methyl-1-piperazinyl)ethyl]-9-acridanone (2-thiazolyl)hydrazone. 2.5 HCl of melting point 230° (decomposition).

In an analogous manner there is obtained:

(b) From 10-[2-(dimethylamino)ethyl]-9-acridanone and 2-thiazolyl-hydrazine hydrochloride, the 10-[2-(dimethylamino)ethyl]-9-acridanone (2-thiazolyl)hydrazone dihydrochloride of melting point >200° (decomposition);

(c) from 10-[2-(4-ethoxycarbonyl-1-piperazinyl)ethyl]-9-acridanone and 2-thiazolyl-hydrazine hydrochloride, the 10-[2-(4-ethoxycarbonyl-1-piperazinyl)ethyl]-9-acridanone (2-thiazolyl)hydrazone dihydrochloride of melting point 185° (decomposition);

(d) from 10-[2-[4-(methylsulphonyl)-1-piperazinyl]ethyl]-9-acridanone and 2-thiazolyl-hydrazine hydrochloride, the 10-[2-([4-(methylsulfonyl)-1-piperazinyl]ethyl]-9-acridanone (2-thiazolyl)hydrazone dihydrochloride of melting point 200°;

(e) from 10-[2-(4-propyl-1-piperazinyl)ethyl]-9-acridanone and 2-thiazolyl-hydrazine hydrochloride, the 10-[2-(4-propyl-1-piperazinyl)ethyl]-9-acridanone (2-thiazolyl)hydrazone. 2.5 HCl of melting point 220° (decomposition).

EXAMPLE 7

(a) A mixture of 9.75 g of 9-acridanone, 200 ml of dimethylformamide and 4.8 g sodium hydride is stirred for 0.5 hour, treated portionwise with 17.8 g of 2-[4-[2-(diethylamino)ethyl]-1-piperazinyl]ethyl chloride trihydrochloride, stirred at 70° for 18 hours, then heated to boiling under reflux for 8 hours and evaporated. The residue is treated with 100 ml of water and extracted with dichloromethane. The extract is washed with water, dried and evaporated. The product is crystallized twice from petroleum ether and there is obtained 10-[2-[4-[2-(diethylamino)ethyl]-1-piperazinyl]ethyl-9-acridanone of melting point 106°–108°.

A suspension of 4.06 g of this substance in 100 ml of dry acetonitrile is treated portionwise while stirring with 1.7 ml of oxalyl chloride and evaporated after 0.5 hour. The residue is treated with acetonitrile and filtered under suction. The material obtained is washed successively with ether and petroleum ether and then dried. The brown powder, 9-chloro-10-[2-[4-[2-(diethylamino)ethyl]-1-piperazinyl]ethyl]acridinium chloride, is taken up in 100 ml of methanol, treated with 1.52 g of 2-thiazolyl-hydrazine hydrochloride and 2.46 g of sodium acetate and heated to boiling under reflux for 10 minutes. After evaporation, the residue is treated with 100 ml of water, made alkaline to phenolphthalein with 2N sodium hydroxide solution, the precipitated product is taken up in 100 ml of dichloromethane, the solution is washed neutral with water, dried and evaporated. The residue is dissolved in 100 ml of methanol and acidified with ethereal hydrochloric acid. The precipitated salt is filtered and washed successively with methanol, ether and petroleum ether. There is obtained 10-[2-[4-[2-(diethylamino)ethyl]-1-piperazinyl]ethyl]-9-acridanone (2-thiazolyl)hydrazone. 3.5 HCl of melting point 235° (decomposition).

In an analogous manner there is obtained:

(b) From 10-[2-[4-[2-(diethylamino)ethyl]-1-piperazinyl]ethyl]-9-acridanone and 2-hydrazino-2-thiazoline hydrobromide, the 10-[2-[4-[2-(diethylamino)ethyl]-1-piperazinyl]ethyl]-9-acridanone (2-thiazolidinylidene)hydrazone of melting point 144°-146° (decomposition).

EXAMPLE 8

(a) A mixture of 4.94 g of 10-[2-(diethylamino)ethyl]-9-acridanone, 300 ml of dichloromethane and 2.85 ml (33.6 mmol) of oxalyl chloride is stirred for 20 minutes, the crystals (9-chloro-10-[2-(diethylamino)ethyl]-acridinium chloride) obtained are filtered with ether. This material is taken up in 100 ml of methanol, treated with 2.8 g of N-methyl-N-(2-thiazolyl)hydrazine hydrochloride and 4.1 g of sodium acetate, heated to boiling under reflux for 15 minutes and evaporated. The residue is made alkaline with sodium carbonate solution, extracted with dichloromethane, the extract is washed with water, dried and evaporated. By crystallization of the residue from isopropyl ether there is obtained 10-[2-(diethylamino)ethyl]-9-acridanone methyl(2-thiazolyl)-hydrazone of melting point 103°-104°.

In an analogous manner there is obtained:

(b) from 10-[2-(diethylamino)ethyl]-9-acridanone and N-methyl-N-(2-thiazolin-2-yl)hydrazone, the 10-[2-(diethylamino)ethyl]-9-acridanone methyl(2-thiazolin-2-yl)hydrazone of melting point 109°-110°.

EXAMPLE 9

A suspension of 58.6 g of 9-acridanone in 200 ml of dimethylformamide, heated to boiling under reflux, is treated portionwise with a total of 60 g of benzyl ethylenecarbamate. After 53 hours, the mixture is left to cool, the crystalline product is filtered and washed successively with dimethylformamide, acetone and ether.

The mother liquor is treated with water, whereupon the precipitated product is filtered and washed as above. The combined material is crystallized from ethanol and there is obtained benzyl [2-(9-oxo-10(9H)-acridinyl)ethyl]carbamate of melting point 224°-226°.

9.31 g of this substance are suspended in 100 ml of dichloromethane. The suspension is treated with 4.5 ml of oxalyl chloride, stirred for 1 hour and the solution is evaporated. The residue is taken up in 400 ml of acetonitrile, treated with 5.55 g of 2-hydrazino-2-thiazoline hydrobromide and heated to boiling under reflux for 24 hours. The still warm mixture is filtered, the material obtained is washed successively with acetonitrile and ether, treated with methylene chloride and water and the base is liberated by the addition of sodium carbonate solution. The free base is purified by chromatography on silica gel while eluting with dichloromethane and it is converted into the hydrochloride with ethanolic hydrochloric acid. By the addition of ether to the solution obtained there is obtained crystalline benzyl [2-[9-(2-thiazolidinylidenehydrazono)-10-acridanyl]ethyl]carbamate dihydrochloride of melting point 167.7°-170.8° (decomposition).

A suspension of 3.5 g of the above substance if 300 ml of glacial acetic acid is stirred for 3 days with 10 ml of hydrogen bromide-containing glacial acetic acid (about 30 percent), whereupon the product is filtered off and washed with glacial acetic acid and ether. It is subsequently taken up in water, the base is liberated with sodium carbonate and taken up in methylene chloride. The methylene chloride solution is dried over sodium sulfate and evaporated. The residue is dissolved in ethanolic hydrogen chloride and the salt is crystallized by the addition of ether. There is obtained 10-(2-aminoethyl)-9-acridanone (2-thiazolidinylidene)hydrazone dihydrochloride of melting point 226°-231°.

EXAMPLE 10

2.25 g of benzyl [2-(9-oxo-10(9H)-acridinyl)-ethyl]-carbamate are suspended in 20 ml of methylene chloride and treated with 1.05 ml of oxalyl chloride. After 1 hour, the solution is evaporated, whereupon the residue is taken up in 200 ml of acetonitrile, treated with 1.09 g of 2-thiazolyl-hydrazine hydrochloride and heated to boiling under reflux for 1.5 hours. The mixture is left to cool, the crystals are filtered under suction and washed with acetonitrile and ether. There is obtained benzyl [2-[9-(2-thiazolylhydrazono)-9-acridanyl]ethyl]carbamate hydrochloride of melting point 207°-209° (decomposition).

A suspension of 7.6 g of this substance in 450 ml of glacial acetic acid is treated with 20 ml of hydrogen bromide-containing glacial acetic acid (about 30 percent) and stirred for 2 days. The product is filtered under suction and washed with glacial acetic acid and ether. The salt mixture is converted into the hydrochloride with a hydrochloric acidic ion exchanger. The aqueous solution is freeze-dried and the crystalline residue is recrystallized repeatedly from methanol/ether. There is obtained 10-(2-aminoethyl)-9-acridanone 2-thiazolylhydrazone dihydrochloride of melting point 204°-214° (decomposition).

EXAMPLE 11

A suspension of 11.2 g of benzyl [2-(9-oxo-10(9H)-acridinyl)ehtyl]carbamate in 100 ml of glacial acetic acid is treated with 20 ml of hydrogen bromide-containing glacial acetic acid (about 30 percent) and stirred for 1 hour. The product is filtered and washed with glacial acetic acid and ether. There is obtained 10-(2-aminoethyl)-9-acridanone hydrobromide of melting point >250°. The free base is precipitated from an aqueous solution with sodium bicarbonate solution, filtered and washed with water and acetone. The hydrochloride obtained therefrom and analyzed melts above 250°.

6.11 g of the above free base are suspended in 100 ml of pyridine, whereupon the suspension is treated with 2.33 ml of methanesulfochloride. While warming there is obtained a clear solution, to which 700 ml of water are added after 3 hours. Crystals form gradually. The mixture is concentrated to 300 ml, 500 ml of water are added thereto and the mixture obtained is concentrated in vacuo to 300 ml. The product is filtered, washed with water and recrystallized from ethanol. There is obtained N-[2-(9-oxo-10-acridanyl)ethyl]methanesulfonamide of melting point 226°-227°.

950 mg of this substance are suspended in 10 ml of methylene chloride, whereupon the suspension is treated with 0.8 ml of oxalyl chloride. After 1 hour, the mixture is evaporated. The residue is taken up in 100 ml of acetonitrile and treated with 713 mg of 2-hydrazino-2-thiazoline hydrobromide. After 20 minutes under reflux, the product is filtered, washed with ether and dissolved in 150 ml of methylene chloride/methanol (97:3). The solution is made alkaline with sodium bicarbonate solution, extracted with methylene chloride, dried over sodium sulfate and evaporated. After crystallization from methylene chloride/methanol/petroleum ether, there is obtained N-[2-[9-(2-thiazolin-2-yl)hydrazono]-10 -acridanyl]-ethyl]methanesulfonamide of melting point 206°–207° (decomposition).

EXAMPLE 12

(a) A suspension of 1.44 g of sodium hydride in 100 ml of dimethylformamide is treated within 10 minutes with 9.75 g of 9-acridanone and held at 50° for 2 hours. At 120° there are then added 9.5 g of 4,4-diethoxybutyl chloride. After 16 hours, the mixture is cooled, poured into water and extracted with dichloromethane. The extract is dried over sodium sulfate and evaporated. The residue is extracted with hexane and crystallized twice from hexane. There is obtained 10-(4,4-diethoxybutyl)-9-acridanone of metling point 73°–74.5°.

8.5 g of this substance are dissolved in 20 ml of diethylamine, whereupon the solution is treated with 15 ml of formic acid, heated to 100° for 20 hours, cooled, water and dilute hydrochloric acid are added and the aqueous solution is washed with ether. The aqueous solution is treated with sodium hydroxide solution and extracted with methylene chloride. The extract is dried over sodium sulphate and evaporated. The residue is crystalized from hexane. There is obtained 10-[4-diethylamino)butyl]-9-acridanone of melting point 66.5°–68.7°. The hydrochloride has a melting point of 126.8°–128.3°.

2.4 ml of oxalyl chloride are added drop-wise at 0° within 3 minutes to a solution of 3.0 g of the above free base in 200 ml of dichloromethane. The mixture is stirred at room temperature for 1 hour and evaporated. The residue, 9-chloro-10-[4-(diethylamino)butyl]-acridinium chloride, is taken up in 300 ml of acetonitrile, treated with 1.57 g of 2-hydrazino-2-thiazoline hydrochloride, heated to boiling under reflux for 0.5 hour, stirred at room temperature for an additional 1.5 hours and cooled to 0°. The product is filtered, washed with acetonitrile and ether and taken up in water. The solution is made alkaline with sodium carbonate and extracted with methylene chloride. The methylene chloride solution is dried over sodium sulfate and evaporated. By crystallization from dichloromethane/ether/petroleum ether there is obtained 10-[4-diethylamino)butyl]-9-acridanone (2-thiazolidinylidene)-hydrazone of melting point 105.6°–107.2°.

In an analogous manner there is obtained:

(b) From 9-acridanone and 5,5-diethoxypentyl chloride, the 10-(5,5-diethoxypentyl)-9-acridanone of melting point 82°–83°, therefrom the 10[5-(diethylamino)-pentyl]-9-acridanone of melting point 59°–61.2° and therefrom the 10-[5-(diethylamino)pentyl]-9-acridanone (2-thiazolidinylidene)hydrazone of melting point 128.5°–130.1°.

EXAMPLE A

Preparation of tablets of the following composition:

|  | mg/tablet |
| --- | --- |
| 10-[2-(4-methyl-1-piperazinyl)ethyl-9-acridanone (2-thiazolyl) hydrazone | 100 |
| Lactose | 100 |
| Maize starch | 85 |
| Povidone | 10 |
| Talc | 3 |
| Magnesium stearate | 2 |
| Tablet weight | 300 mg |

The active substance is mixed with the lactose and the maize starch, moistened with an aqueous solution of Povidone and granulated. The granulate is dried at 40° and sieved. The sieved granulate is mixed with the talc and magnesium stearate and the mixture is pressed to tablets.

The following compounds of formula I can be processed, for example, as the active substance as described above:

10-[2-(4-methyl-1-piperazinyl)ethyl]-9-acridanone (2-thiazolidinylidene)hydrazone, 10-[2-(4-acetyl-1-piperazinyl)ethyl]-9-acridanone (2-thiazolidinylidene)hydrazone, 10-[2-(dimethylamino)ethyl]-9-acridanone (2-thiazolidinylidene)hydrazone, 10-[2-(diethylamino)ethyl]-9-acridanone (2-thiazolyl)hydrazone, 10-[2-(1-piperadinyl)ethyl]-9-acridanone (2-thiazolyl)hydrazone, 10-(2-aminoethyl)-9-acridanone (2-thiazolyl)hydrazone, 10-[2-(dimethylamino)ethyl]-9-acridanone (2-thiazolyl)hydrazone, 10-[2-(4-acetyl-1-piperazinyl)ethyl]-9-acridanone (2-thiazolyl)hydrazone, 10-[3-(dimethylamino)propyl]-9-acridanone (2-thiazolyl)hydrazone, 10-[2-(diethylamino)ethyl]-9-acridanone (2-thiazolidinylidene)hydrazone, 10-[2-(1-pyrrolidinyl)ethyl]-9-acridanone (2-thiazolidinylidene)hydrazone and 10-[3-(dimethylamino)propyl]-9-acridanone (2-thiazolidinylidene)hydrazone.

We claim:

1. A compound of the formula

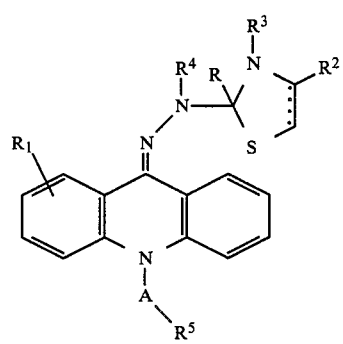

wherein the dotted line is an optional bond, $R^1$ is hydrogen, halogen or nitro, $R^2$ is hydrogen or lower alkyl, one of $R^3$ and $R^4$ is hydrogen or lower alkyl and the other together with R is an additional bond, A is lower alkylene, R⁵ is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle, amino or the group

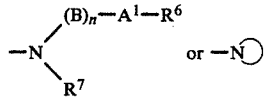

the symbol

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B—)$_n$—A¹—R⁶; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A¹—R⁶ wherein B is —CO—, —COO— or —SO₂—, n is the integer 0 or 1, A¹ is lower alkylene, R⁶ is hydrogen, amino, lower alkylamino or di(lower alkyl) amino and R⁷ is hydrogen or lower alkyl, or a pharmaceutically acceptable acid addition salt thereof.

2. A compound in accordance with claim 1, wherein R¹ and R² are hydrogen.

3. A compound in accordance with claim 1, wherein R¹ is situated in the 1-position.

4. A compound in accordance with claim 3, wherein R¹ is hydrogen.

5. A compound in accordance with claim 4, wherein R² is hydrogen.

6. A compound in accordance with claim 5, wherein one of R³ and R⁴ is hydrogen and the other together with R is an additional bond.

7. A compound in accordance with claim 6, wherein A is dimethylene or trimethylene.

8. A compound in accordance with claim 7, wherein R⁵ is amino, 1-pyrrolidinyl, 1-piperidinyl, 1-morpholinyl, 1-piperazinyl or the group

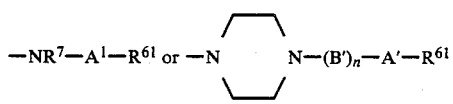

in which A' is lower alkylene, B' is the group —CO—, n is the integer 0 or 1, R⁶¹ is hydrogen and R⁷ is hydrogen or lower alkyl.

9. A compound in accordance with claim 7, wherein R⁵ is amino, dimethylamino, diethylamino, 1-pyrrolidinyl, 1-piperidinyl, 4-methyl-1-piperazinyl or 4-acetyl-1-piperazinyl.

10. A compound in accordance with claim 1, 10-[2-(4-(methyl-1-piperazinyl)ethyl]-9-acridanone (2-thiazolyl)-hydrazone.

11. A compound in accordance with claim 1, 10-[2-(4-methyl-1-piperazinyl)ethyl]-9-acridanone (2-thiazolidinylidene)hydrazone.

12. A compound in accordance with claim 1, 10-[2-(4-acetyl-1-piperazinyl)ethyl]-9-acridanone (2-thiazolidinylidene)hydrazone.

13. A compound in accordance with claim 1, 10-[2-(dimethylamino)ethyl]-9-acridanone (2-thiazolidinylidene)hydrazone.

14. A comound in accordance with claim 1, 10-[2-(diethylamino)ethyl]-9-acridanone (2-thiazolyl)hydrazone.

15. A compound in accordance with claim 1, 10-[2-(1-piperidinyl)ethyl]-9-acridanone (2-thiazolyl)hydrazone.

16. A compound in accordance with claim 1, 10-(2-aminoethyl)-9-acridanone (2-thiazolyl)hydrazone.

17. A compound in accordance with claim 1, 10-[2-(dimethylamino)ethyl]-9-acridanone (2-thiazolyl)hydrazone.

18. A compound in accordance with claim 1, 10-[2-(4-acetyl-1-piperazinyl)ethyl]-9-acridanone (2-thiazolyl)-hydrazone.

19. A compound in accordance with claim 1, 10-[3-(dimethylamino)propyl]-9-acridanone (2-thiazolyl)hydrazone.

20. A compound in accordance with claim 1, 10-[2-(diethylamino)ethyl]-9-acridanone (2-thiazolidinylidene)hydrazone.

21. A compound in accordance with claim 1, 10-[2-(1-pyrrolidinyl)ethyl]-9-acridanone (2-thiazolidinylidene)-hydrazone.

22. A compound in accordance with claim 1, 10-[3-(dimethylamino)propyl]-9-acridanone (2-thiazolidinylidene)hydrazone.

23. A compound selected from the group consisting of

10-[2-(4-Propyl-1-piperazinyl)ethyl]-9-acridanone (2-thiazolidinylidene)hydrazone,
10-[2-(dimethylamino)propyl]-9-acridanone (2-thiazolidinylidene)hydrazone,
10-[2-(1-piperidinyl)ethyl]-9-acridanone (2-thiazolidinylidene)hydrazone,
10-[2-(2,6-dimethyl-1-piperidinyl)ethyl]-9-acridanone (2-thiazolidinylidene)hydrazone,
10-[2-(4-morpholinyl)ethyl]-9-acridanone (2-thiazolidinylidene)hydrazone,
10-[2-(4-ethoxycarbonyl-1-piperazinyl)ethyl]-9-acridanone (2-thiazolidinylidene)hydrazone,
10-[2-(4-pivaloyl-1-piperazinyl)ethyl]-9-acridanone (2-thiazolidinylidene)hydrazone,
10-[2-[4-(methylsulfonyl)-1-piperazinyl]ethyl]-9-acridanone (2-thiazolidinylidene)hydrazone,
10-[(1-methyl-4-imidazolyl)methyl]-9-acridanone (2-thiazolidinylidene)hydrazone,
10-[2-[4-[2-(dimethylamino)acetyl]-1-piperazinyl]ethyl]-9-acridanone (2-thiazolidinylidene)hydrazone,
1-chloro-10-[2-(diethylamino)ethyl]-9-acridanone (2-thiazolidinylidene)hydrazone,
10-(2-aminoethyl)-9-acridanone (2-thiazolidinylidene)-hydrazone,
10-[2-[(methylsulfonyl)amino]ethyl]-9-acridanone (2-thiazolidinylidene)hydrazone,
10-[4-(diethylamino)butyl]-9-acridanone (2-thiazolidinylidene)hydrazone,
10-[5-(diethylamino)pentyl]-9-acridanone (2-thiazolidinylidene)hydrazone,
10-[2-(diethylamino)ethyl]-9-acridanone methyl(2-thiazolin-2-yl)hydrazone and
10-[2-(diethylamino)ethyl-9-acridanone (3-methyl-2-thiazolidinylidene)hydrazone.

24. A compound selected from the group consisting of
10-[2-(Diethylamino)ethyl]-9-acridanone methyl-(2-thiazolyl)hydrazone,
10-[2-(4-morpholinyl)ethyl]-9-acridanone (2-thiazolyl)-hydrazone,
10-[2-(4-ethoxycarbonyl-1-piperazinyl)ethyl-9-acridanone (2-thiazolyl)hydrazone,
10-[2-(4-pivaloyl-1-piperazinyl)ethyl]-9-acridanone (2-thiazolyl)hydrazone,
10-[2-[4-(methylsulfonyl)-1-piperazinyl]ethyl]-9-acridanone (2-thiazolyl)hydrazone,
10-[2-[4-[2-(diethylamino)ethyl]-1-piperazinyl]ethyl]-9-acridanone (2-thiazolyl)hydrazone and
10-[2-(4-propyl-1-piperazinyl)ethyl]-9-acridanone (2-thiazolyl)hydrazone.

25. A schistosomicidal composition comprising a schistosomicidally effective amount of a compound of the formula

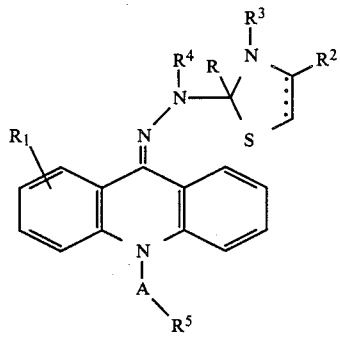   I wherein the dotted line is an optional bond,
R$^1$ is hydrogen, halogen or nitro,
R$^2$ is hydrogen or lower alkyl,
one of R$^3$ and R$^4$ is hydrogen or lower alkyl and the other together with R is an additional bond,
A is lower alkylene, R$^5$ is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle, amino or the group

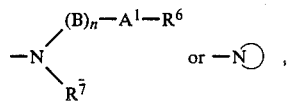

the symbol

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$ wherein B is —CO—, —COO— or —SO$_2$—, n is the integer 0 or 1, A$^1$ is lower alkylene, R$^6$ is hydrogen, amino, lower alkyl-amino or di(lower alkyl) amino and R$^7$ is hydrogen or lower alkyl, or a pharmaceutically acceptable acid addition salt thereof, and an inert pharmaceutical carrier.

26. A compound of the formula

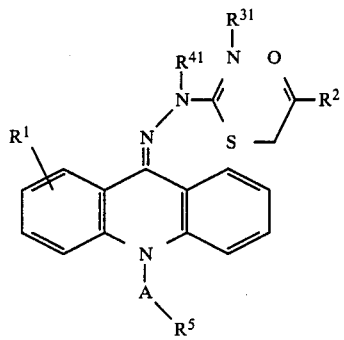   II wherein R$^1$ is hydrogen, halogen or nitro,
R$^2$ is hydrogen or lower alkyl,
one of R$^{31}$ and R$^{41}$ is hydrogen or lower alkyl and the other is hydrogen,
A is lower alkylene,
R$^5$ is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle, amino or the group

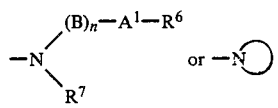

the symbol

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$ wherein B is —CO—, —COO— or —SO$_2$—, n is the integer 0 or 1, A$^1$ is lower alkylene, R$^6$ is hydrogen, amino, lower alkyl-amino or di(lower alkyl) amino and R$^7$ is hydrogen or lower alkyl.

27. A compound of the formula

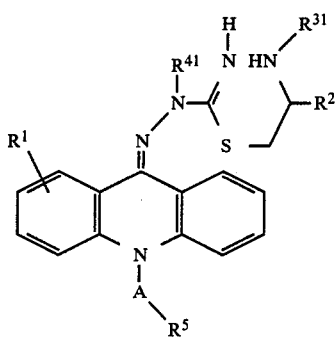

wherein R[1] is hydrogen, halogen or nitro,
R[2] is hydrogen or lower alkyl,
one of R[31] and R[41] is hydrogen or lower alkyl and the other is hydrogen,
A is lower alkylene,
R[5] is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle, amino or the group

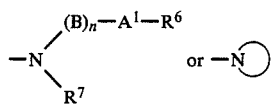

the symbol

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B-)$_n$—A[1]—R[6]; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A[1]—R[6] wherein B is —CO—, —COO— or —SO$_2$—, n is the integer 0 or 1, A[1] is lower alkylene, R[6] is hydrogen, amino, lower alkylamino or di(lower alkyl) amino and R[7] is hydrogen or lower alkyl.

28. A compound of the formula

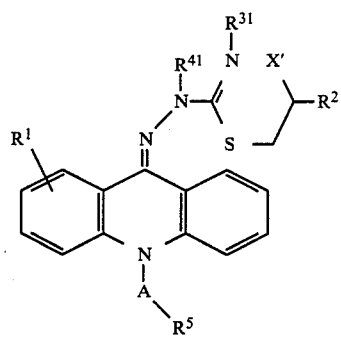

IV wherein R[1] is hydrogen, halogen or nitro,
R[2] is hydrogen or lower alkyl,
one of R[31] and R[41] is hydrogen or lower alkyl and the other is hydrogen,
X[1] is halogen, A is lower alkylene,
R[5] is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle, amino or the group

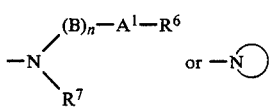

the symbol

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B-)$_n$—A[1]—R[6]; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A[1]—R[6] wherein B is —CO—, —COO— or —SO$_2$—, n is the integer 0 or 1, A[1] is lower alkylene, R[6] is hydrogen, amino, lower alkylmino or di(lower alkyl) amino and R[7] is hydrogen or lower alkyl.

29. A compound of the formula

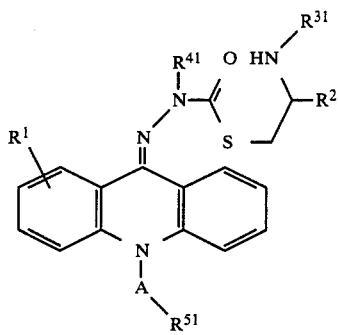

V wherein R[1] is hydrogen, halogen or nitro,
R[2] is hydrogen or lower alkyl,
one of R[31] and R[41] is hydrogen or lower alkyl and the other is hydrogen,
A is lower alkylene,
R[51] is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle or the group $$-N\diagdown_{R^7}^{(B)_n-A^1-R^6} \quad \text{or} \quad -N\bigcirc$$

the symbol $$-N\bigcirc$$

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$ wherein B is the group —CO—, —COO— or —SO$_2$—, n is the integer 0 or 1, A$^1$ is lower alkylene, R$^6$ is hydrogen or di(lower alkyl) amino and R$^7$ is hydrogen or lower alkyl provided R$^{51}$ does not contain a secondary basic amino group.

30. A compound of the formula

VI

[structure with R$^1$, R$^{42}$, R$^2$, X', S, N, A, R$^{51}$]

wherein R$^1$ is hydrogen, halogen or nitro,
R$^2$ is hydrogen or lower alkyl,
R$^{42}$ is hydrogen or lower alkyl,
X$^1$ is halogen,
A is lower alkylene,
R$^{51}$ is a 5-membered optionally lower alkyl substituted, aromatic heterocycle, containing one or two nitrogen atoms or one nitrogen atom and an oxygen or sulfur atom linked with group A via a carbon atom or via a nitrogen of the heterocycle or the group $$-N\diagdown_{R^7}^{(B)_n-A^1-R^6} \quad \text{or} \quad -N\bigcirc$$

the symbol $$-N\bigcirc$$

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$ wherein B is the group —CO—, —COO— or —SO$_2$—, n is the integer 0 or 1, A$^1$ is lower alkylene, R$^6$ is hydrogen or di(lower alkyl) amino and R$^7$ is hydrogen or lower alkyl provided R$^{51}$ does not contain a secondary basic amino group.

31. A compound of the formula

VII

[structure with R$^1$, R$^{42}$, R$^2$, H, O, S, N, A, R$^{51}$]

wherein R$^1$ is hydrogen, halogen or nitro,
R$^2$ is hydrogen or lower alkyl,
R$^{42}$ is hydrogen or lower alkyl, A is lower alkylene,
R$^{51}$ is a 5-membered, optionally lower alkyl-substituted aromatic heterocycle, containing one or two nitrogen atoms or one nitrogen atom and an oxygen or sulfur atom linked with group A via a carbon atom or via a nitrogen of the heterocycle or the group $$-N\diagdown_{R^7}^{(B)_n-A^1-R^6} \quad \text{or} \quad -N\bigcirc$$

the symbol $$-N\bigcirc$$

is an unsubstituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group —(B)$_n$—A$^1$—R$^6$ wherein B is the group —CO—, —COO— or —SO$_2$—, n is the integer 0 or 1, A$^1$ is lower alkylene, R$^6$ is hydrogen or di(lower alkyl) amino·and R$^7$ is hydrogen or lower alkyl provided R$^{51}$ does not contain secondary basic amino group.

32. A compound of the formula

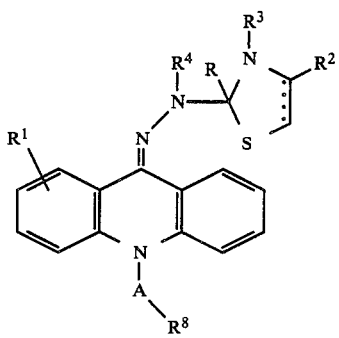

wherein the dotted line is an optional bond $R^1$ is hydrogen, halogen or nitro, $R^2$ is hydrogen or lower alkyl, one of $R^3$ and $R^4$ is hydrogen or lower alkyl and the other together with R is an additional bond, A is lower alkylene, $R^8$ is a 5-membered, nitrogen-containing, optionally lower alkyl-substituted aromatic heterocycle, containing one or two nitrogen atoms or one nitrogen atom and an oxygen or sulfur atom linked with group A via a carbon atom or via a nitrogen of the heterocycle amino or the group XII 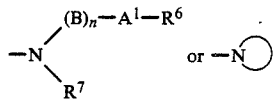 or 

the symbol $-N\bigcirc$ is an unsubstituted heterocycle selected from the group consisting of 1-pyrrolidinyl, 1-piperidinyl, 4-morpholino, 1-piperazinyl and 1-piperazinyl substituted on the second nitrogen atom by the group $-(B)_n-A^1-R^6$; or a lower-alkyl substituted heterocycle selected from the group consisting of 1-pyrrolidinyl, 1-piperidinyl, 4-morpholino, 1-piperazinyl and 1-piperazinyl substituted on the second nitrogen atom by the group $-(B)_n-A^1-R^6$ wherein B is $-CO-$, $-COO-$ or $-SO_2-$, n is the integer 0 or 1, $A^1$ is lower alkylene, $R^6$ is hydrogen, amino, lower alkylamino or di(lower alkyl) amino and $R^7$ is hydrogen or lower alkyl provided that a primary or secondary basic amino group is blocked by an acyl or phenylalkyl group.

33. A composition in accordance with claim 25, wherein $R^1$ is in the 1-position.

34. A composition in accordance with claim 25, wherein the compound of formula I is 10-[2-(diethylamino)ethyl]-9-acridanone (2-thiazolyl)hydrazone or the hydrochloride salt thereof.

* * * * *